United States Patent [19]

Anthony et al.

[11] Patent Number: 4,812,162
[45] Date of Patent: Mar. 14, 1989

[54] INDOLE DERIVATIVES AND THEIR USE AS FUNGICIDES, INSECTICIDES AND PESTICIDES

[75] Inventors: Vivienne M. Anthony, Maidenhead; John M. Clough, Marlow; Christopher R. A. Godfrey, Bracknell; Paul J. de Fraine, Wokingham, all of United Kingdom

[73] Assignee: Imperial Chemical Industries PLC, London, England

[21] Appl. No.: 123,212

[22] Filed: Nov. 20, 1987

[30] Foreign Application Priority Data

Dec. 5, 1986 [GB] United Kingdom ............... 8629169

[51] Int. Cl.$^4$ ............ A01N 43/10; A01N 43/28; A01N 43/38; C07D 209/04; C07D 401/06; C07D 403/06; A61K 31/38; A61K 31/405

[52] U.S. Cl. .................................. 71/90; 71/92; 71/94; 71/95; 71/96; 514/256; 514/333; 514/339; 514/365; 514/414; 514/415; 544/296; 544/333; 546/256; 546/273; 548/430; 548/466; 548/505; 548/510

[58] Field of Search ............... 548/430, 466, 494, 505, 548/510, 30; 546/256, 273; 544/296, 333; 71/90, 92, 94, 95, 96; 514/256, 333, 339, 365, 414, 415

[56] References Cited

PUBLICATIONS

Heterocyclic Chemistry, J. A. Joule & G. F. Smith, pp. 1, 4 & 5 (1984).

Primary Examiner—Mary C. Lee
Assistant Examiner—J. Richter
Attorney, Agent, or Firm—Cushman, Darby & Cushman

[57] ABSTRACT

Compounds of the formula:

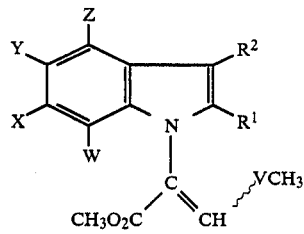

and stereoisomers thereof, wherein $R^1$ and $R^2$, which are the same or different, are hydrogen, cyano or halogen (fluorine, chlorine, bromine or iodine) or optionally substituted alkyl; V is either oxygen or sulphur; W, X, Y and Z, which may be the same or different, are hydrogen, halogen, nitro, cyano, optionally substituted alkyl, optionally substituted cycloalkyl, optionally substituted cycloalkylalkyl, optionally substituted aralkyl, optionally substituted aryl, optionally substituted aryloxy, optionally substituted alkoxy, optionally substituted arylalkoxy, optionally substituted alkenyl $S(O)_nR^3$ (wherein n is 0, 1 or 2), or optionally substituted heteroaryl, or W, X or X, Y or Y, Z together form methylenedioxy; and $R^3$ is optionally substituted alkyl, optionally substituted aryl, optionally substituted aralkyl or optionally substituted heteroaryl. The compounds are useful as fungicides and also as plant growth regulators, insecticides and miticides.

9 Claims, No Drawings

INDOLE DERIVATIVES AND THEIR USE AS FUNGICIDES, INSECTICIDES AND PESTICIDES

This invention relates to derivatives of acrylic acid useful in agriculture (especially as fungicides but also as plant growth regulators, insecticides and miticides), to processes for preparing them, to agricultural (especially fungicidal) compositions containing them, and to methods of using them to combat fungi (especially fungal infections in plants), to regulate plant growth and to control or kill insects and mites.

The invention provides a compound having the general formula (I):

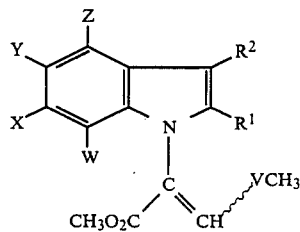

and stereoisomers thereof, wherein $R^1$ and $R^2$, which are the same or different, are hydrogen, cyano or halogen (fluorine, chlorine, bromine or iodine) or optionally substituted alkyl; V is either oxygen or sulphur; W, X, Y and Z, which may be the same or different, are hydrogen, halogen, nitro, cyano, optionally substituted alkyl, optionally substituted cycloalkyl, optionally substituted cycloalkylalkyl, optionally substituted aralkyl, optionally substituted aryl, optionally substituted aryloxy, optionally substituted alkoxy, optionally substituted arylalkoxy, optionally substituted alkenyl, $S(O)_nR^3$ (wherein n is 0, 1 or 2), or optionally substituted heteroaryl, such as pyridyl, or W, X or X, Y or Y, Z together form methylenedioxy; and $R^3$ is optionally substituted alkyl, optionally substituted aryl, optionally substituted aralkyl or optionally substituted heteroaryl.

The compounds of the invention contain at least one carbon-carbon double bond, and are sometimes obtained in the form of mixtures of geometric isomers. However, these mixtures can be separated into individual isomers, and this invention embraces such isomers individually and mixtures thereof in all proportions including those which consist substantially of the (E)-isomer and those which consist substantially of the (Z)-isomer.

The individual isomers, which results from the unsymmetrically substituted double bond of the acrylate group, are identified by the commonly used terms "E" and "Z". These terms are defined according to the Cahn-Ingold-Prelog system which is fully described in the literature (see, for example, J March, "Advanced Organic Chemistry," 3rd edition, Wiley-Interscience, page 109 et seq).

Usually one isomer is more fungicidally active than the other; the more active isomer being the one in which the group —VCH₃ is on the same side of the double bond as the indole ring. In the case of the compounds of the present invention this is the (Z)-isomer. These isomers form a preferred embodiment of the invention.

The formula:

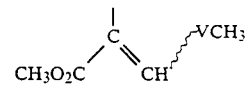

is used herein to signify a separable mixture of both geometric isomers about the acrylate double bond, i.e.

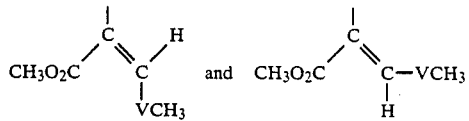

Alkyl groups and the alkyl moieties of alkoxy groups preferably contain from 1 to 6, especially 1 to 4 carbon atoms, and can be in the form of straight or branched chains. Examples are methyl, ethyl, propyl (n- and isopropyl) and butyl (n-, sec-, iso- and tert-butyl).

Preferred cycloalkyl groups contain from 3 to 6 carbon atoms, i.e. cyclopropyl, cyclobutyl, cyclopentyl and cyclohexyl. Cycloalkylalkyl is preferably $(C_{3-6})$cycloalkyl$(C_{1-6})$alkyl, for example, 1-cyclopropylethyl.

Optional substituents of alkyl, cycloalkyl, cycloalkylalkyl and alkoxy include hydroxy and halogen (especially chlorine or fluorine), $C_{1-4}$ alkoxy and $C_{1-4}$ alkoxycarbonyl. Examples of substituted alkyl and alkoxy are trifluoromethyl and trifluoromethoxy.

Aryl groups and the aryl moieties of aryloxy groups may be unsubstituted or substituted with 1, 2 or 3 ring substituents at, in the case of phenyl (a preferred aryl group) the 2-, 3- or 4-positions of the ring. Such substituents, which may be the same or different, include halogen (especially chlorine or fluorine), hydroxy, alkyl, trifluoroalkyl, alkoxy and trifluoromethoxy. Examples of optionally substituted aryl are phenyl, 2-, 3- or 4-chlorophenyl, 2,4- or 3,5-dichlorophenyl, 2,4- or 3,5-difluorophenyl, 2-, 3- or 4-fluorophenyl, 2-, 3- or 4-methoxyphenyl, 2,4-dimethoxyphenyl, 2-fluoro-4-chlorophenyl, 2-, 3- or 4-methylphenyl, and 2-, 3- or 4-trifluoromethylphenyl.

Aralkyl groups and the aralkyl moieties of arylalkoxy groups include, particularly, phenyl$(C_{1-4})$alkyl (especially benzyl, phenethyl, or phenpropyl) in which the alkyl and aryl moieties may be substituted in the same way as the alkyl and aryl groups described above.

Alkenyl groups preferably contain 2 to 6 carbon atoms, and more preferably, 2 to 4 carbon atoms in the form of straight or branched chains; ethenyl, propenyl and butenyl are examples. Optional substituents of alkenyl groups include aromatic and heteroaromatic groups (such as phenyl, furyl, thienyl and pyridyl) which may themselves be substituted in the same way as the aryl groups above.

Heteroaryl includes pyridyl, pyrimidinyl, thienyl, furyl and pyrrolyl. Optional substituents include those described for the aryl groups above.

In one particular aspect, the invention provides compounds having the general formula (I) and stereoisomers thereof, wherein $R^1$ and $R^2$ which are the same or different, are hydrogen, cyano, halogen, or optionally substituted alkyl; V is oxygen; W, Y and Z, which may be the same or different, are hydrogen, halogen, nitro, cyano, trifluoromethyl or other optionally substituted alkyl, optionally substituted alkoxy, or optionally substituted alkenyl, and X is optionally substituted aryl (especially phenyl), optionally substituted heteroaryl, or optionally substituted aryloxy, or W, X or X, Y or Y, Z together form methylenedioxy. The (Z)-isomer is the preferred isomer. Preferred alkyl, alkoxy, alkenyl, aryl, heteroaryl and aryloxy groups and their optional substituents are the same as those described above.

The invention is illustrated by the compounds listed in Table I which follows. Throughout Table I, compounds have the (Z)-configuration.

TABLE II

SELECTED PROTON NMR DATA
Table II shows selected proton NMR data for certain compounds described in Table I. Chemical shifts are measured in ppm from tetramethylsilane, and deuterochloroform was used as solvent throughout. The following abbreviations are used:

| br = broad | t = triplet |
| s = singlet | q = quartet |
| d = doublet | m = multiplet |
| J = coupling constant | Hz = Hertz |

| COMPOUND NO. | NMR DATA |
|---|---|
| 1 | 3.80(3) s, 3.93(3) s, 6.7–7.5(6) m, 7.78(1) s. |
| 2 | 1.41(3) t, 3.72(3) s, 3.85(3) s, 4.04(2) q, 6.55(2) m, 6.78(1) m, 6.90(1) d, 7.46(1) d, 7.71(1) s. |
| 3 | 3.74(3) s, 3.88(3) s, 6.63(1) m, 7.05(1) m, 7.2–7.7(8) m, 7.77(1) s. |
| 4 | 3.72(3) s, 3.80(3) s, 3.84(3) s, 6.55(2) m, 6.8(1) m, 6.92(1) m, 7.5(1) d, 7.72(1) s. |

TABLE I

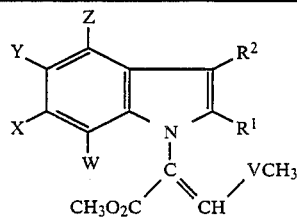

(I)

| COMPOUND NO. | R¹ | R² | V | W | X | Y | Z | MELTING POINT (°C.) | OLEFINIC* |
|---|---|---|---|---|---|---|---|---|---|
| 1 | H | H | O | H | H | H | H | Oil | 7.78 |
| 2 | H | H | O | H | C₂H₅O | H | H | 91–92 | 7.71 |
| 3 | H | H | O | H | C₆H₅ | H | H | 158–160 | 7.77 |
| 4 | H | H | O | H | CH₃O | H | H | Oil | 7.72 |
| 5 | H | H | O | H | Cl | H | H | | |
| 6 | H | H | O | H | CH₃ | H | H | | |
| 7 | H | H | O | H | Br | H | H | 125–127 | 7.73 |
| 8 | H | H | O | H | I | H | H | 105–107 | 7.73 |
| 9 | H | H | O | H | CH₃O | CH₃O | H | | |
| 10 | H | H | O | H | OCH₂O | | H | 139–141 | 7.69 |
| 11 | H | H | O | H | C₆H₅—CH₂O | H | H | | |
| 12 | H | H | O | H | NO₂ | H | H | | |
| 13 | H | H | O | H | CN | H | H | | |
| 14 | CH₃ | H | O | H | H | H | H | | |
| 15 | H | CH₃ | O | H | H | H | H | | |
| 16 | H | H | O | H | 4-Cl—C₆H₄ | H | H | | |
| 17 | H | H | O | H | 3-Cl—C₆H₄ | H | H | | |
| 18 | H | H | O | H | 2-Cl—C₆H₄ | H | H | | |
| 19 | H | H | O | H | 2-pyridyl | H | H | | |
| 20 | H | H | O | H | 3-pyridyl | H | H | | |
| 21 | H | H | O | H | 4-pyridyl | H | H | | |
| 22 | H | H | O | H | C₆H₅O | H | H | 108–111 | 7.66 |
| 23 | H | H | O | H | 4-Cl—C₆H₄O | H | H | | |
| 24 | H | H | O | H | 3-Cl—C₆H₄O | H | H | | |
| 25 | H | H | O | H | 2-Cl—C₆H₄O | H | H | | |
| 26 | H | H | O | H | 4-F—C₆H₄ | H | H | | |
| 27 | H | H | O | H | 3-F—C₆H₄ | H | H | | |
| 28 | H | H | O | H | 2-F—C₆H₄ | H | H | | |
| 29 | H | H | O | H | 3,5-di-Cl—C₆H₃ | H | H | | |
| 30 | H | H | O | H | 4-CH₃—C₆H₄ | H | H | | |
| 31 | H | H | O | H | 3-CH₃—C₆H₄ | H | H | | |
| 32 | H | H | O | H | 2-CH₃—C₆H₄ | H | H | | |
| 33 | H | H | O | H | 4-CH₃O—C₆H₄ | H | H | | |
| 34 | H | H | O | H | 3-CH₃O—C₆H₄ | H | H | | |
| 35 | H | H | O | H | 2-CH₃O—C₆H₄ | H | H | | |
| 36 | H | H | O | H | CH₃S | H | H | | |
| 37 | H | H | S | H | H | H | H | | |
| 38 | H | H | O | CH₃ | H | H | H | | |
| 39 | H | H | O | H | H | CH₃ | H | | |
| 40 | H | H | O | H | H | H | CH₃ | | |

Key:
*Chemical shift of singlet from olefinic proton on beta-alkoxyacrylate or beta(alkylthio)acrylate group (ppm from tetramethylsilane).
Solvent: CDCl₃.

TABLE II-continued
SELECTED PROTON NMR DATA
Table II shows selected proton NMR data for certain compounds described in Table I. Chemical shifts are measured in ppm from tetramethylsilane, and deuterochloroform was used as solvent throughout. The following abbreviations are used:

| br = broad | t = triplet |
|---|---|
| s = singlet | q = quartet |
| d = doublet | m = multiplet |
| J = coupling constant | Hz = Hertz |

| COMPOUND NO. | NMR DATA |
|---|---|
| 7 | 3.73(3) s, 3.88(3) s, 6.57(1) m, 6.99(1) m, 7.23(2) m, 7.4–7.5(1) d, 7.73(1) s. |
| 8 | 3.75(3) s, 3.89(3) s, 6.56(1) m, 6.94(1) m, 7.38(2) m, 7.43(1) m, 7.73(1) s. |
| 22 | 3.72(3) s, 3.86(3) s, 6.60(1) m, 6.75(1) m, 6.8–7.6(8) m, 7.66(1) s. |

The compounds of the invention having the general formula (I) where V is oxygen can be prepared from indoles of general formula (II) by the steps shown in Scheme I. Throughout Scheme I the terms $R^1$, $R^2$, W, X, Y and Z are as defined above, and L is a leaving group such as a halide (iodide, bromide or chloride) or a $CH_3SO_4-$ anion.

treatment with a suitable reagent of general formula $CH_3L$ in a suitable solvent, as a subsequent step.

Compounds of general formula (III) can be prepared by treatment of indoles of general formula (II) with a suitable base such as sodium hydride or potassium tert-butoxide and a substituted acetic ester of general formula $LCH_2CO_2CH_3$ in a suitable solvent.

Compounds of general formula (I) in which V is sulphur may be obtained by treating compounds of general formula (IV) with a suitable reagent of general formula $R^4SO_2Cl$, where $R^4$ is alkyl or optionally substituted aryl, in a suitable solvent and then treating the intermediate sulphonates thus formed with a reagent of formula $CH_3SM$ wherein M is an alkali metal such as sodium. Alternatively, compounds of formula (IV) may be treated with a chlorinating reagent such as phosphorus pentachloride, the intermediate 3-chloroacrylates thus formed then being treated with the reagent $CH_3SM$ to give compounds of the invention of formula (I) wherein V is sulphur.

Indoles of general formula (II) can be prepared by standard methods described in the chemical literature (see for example, M P Moyer, J F Shiurba and H Rapoport, *J. Organic Chemistry*, 1986, 51, 5106 and references therein). In further aspects, the invention includes processes as hereinbefore described for preparing the compounds of the invention and the intermediate compounds having the formulae (III) and (IV) used therein.

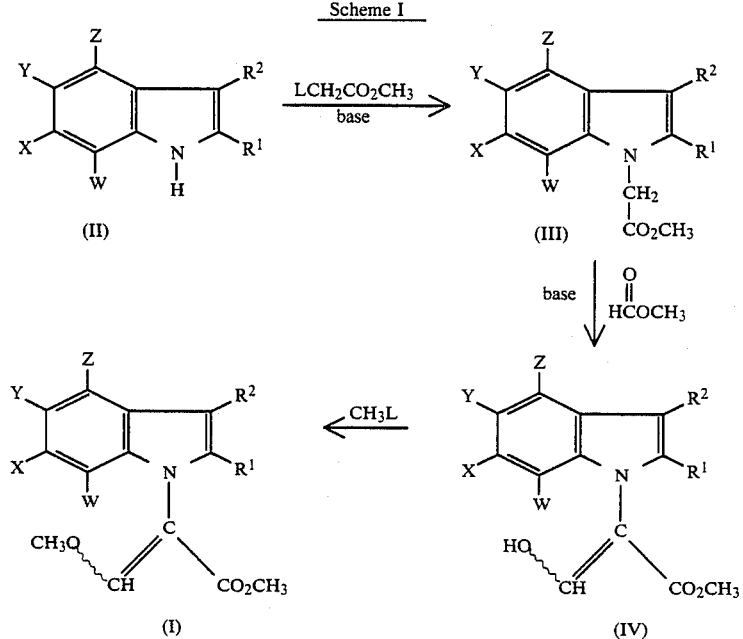

Scheme I

Thus compounds of general formula (I) can be prepared by treatment of substituted acetic esters of general formula (III) with a base and methyl formate, in a suitable solvent, and then quenching the reaction mixture with a suitable species of general formula $CH_3L$.

Alternatively, compounds of general formula (IV) may be isolated by quenching the reaction with water or an acid. In such cases, conversion into compounds of general formula (I) is performed in a separate step by treatment with a suitable base (such as sodium carbonate or potassium carbonate) and a suitable reagent of general formula $CH_3L$ in a suitable solvent.

As another alternative, alkali metal salts of compounds of general formula (IV) may be isolated and converted into compounds of general formula (I) by The compounds of the invention are active fungicides and may be used to control one or more of the following pathogens:

*Pyricularia oryzae* on rice.
*Puccinia recondita, Puccinia striiformis* and other rusts on wheat, *Puccinia hordei, Puccinia striiformis* and other rusts on barley, and rusts on other hosts e.g. coffee, pears, apples, peanuts, vegetables and ornamental plants.
*Erysiphe graminis* (powdery mildew) on barley and wheat and other powdery mildews on various hosts such as *Sphaerotheca macularis* on hops, *Sphaerotheca*

*fuliginea* on cucurbits (e.g. cucumber), *Podosphaera leucotricha* on apple and *Uncinula necator* on vines.

Helminthosporium spp., Rhynchosporium spp., Septoria spp., *Pseudocercosporella herpotrichoides* and *Gaeumannomyces graminis* on cereals.

*Cercospora arachidicola* and *Cercosporidium personata* on peanuts and other Cercospora species on other hosts for example sugar beet, bananas, soya beans and rice.

*Botrytis cinerea* (grey mould) on tomatoes, strawberries, vegetables, vines and other hosts.

Alternaria species on vegetables (e.g. cucumber), oilseed rape, apples, tomatoes and other hosts.

*Venturia inaequalis* (scab) on apples.

*Plasmopara viticola* on vines.

Other downy mildews such as *Bremia lactucae* on lettuce, Peronospora spp. on soybeans, tobacco, onions and other hosts and *Pseudoperonospora humuli* on hops and *Pseudoperonospora cubensis* on cucurbits.

*Phytophthora infestans* on potatoes and tomatoes and other Phytophthora spp. on vegetables, strawberries, avocado, pepper, ornamentals, tobacco, cocoa and other hosts.

*Thanatephorus cucumeris* on rice and other Rhizoctonia species on various host such as wheat and barley, vegetables, cotton and turf.

Some of the compounds show a broad range of activities against fungi in vitro. They may also have activity against various post-harvest diseases of fruit (e.g. *Penicillium digitatum* and *italicum* and *Trichoderma viride* on oranges, *Gloeosporium musarum* on bananas and *Botrytis cinerea* on grapes).

Further some of the compounds may be active as seed dressings against Fusarium spp., Septoria spp., Tilletia spp., (bunt, a seed borne disease of wheat), Ustilago spp., Helminthosporium spp. on cereals, *Rhizoctonia solani* on cotton and *Pyricularia oryzae* on rice.

The compounds can move acropetally and locally in the plant tissue. Moreover, the compounds may be volatile enough to be active in the vapour phase against fungi on the plant.

The invention therefore provides a method of combating fungi, which comprises applying to a plant, to a seed of a plant, or to the locus of the plant or seed, a fungicidally effective amount of a compound as hereinbefore defined, or a composition containing the same.

The compounds may also be useful as industrial (as opposed to agricultural) fungicides, e.g. in the prevention of fungal attack on wood, hides, leather and especially paint films.

Some of the compounds exhibit insecticidal activity and, at appropriate rates of application, may be used to combat a range of insect, nematode and mite pests.

Therefore in another aspect of the invention there is provided a method of killing or controlling insect and mite pests which comprises administering to the pest or to the locus thereof an insecticidally, nematocidally or miticidally effective amount of a compound as hereinbefore defined or a composition containing the same. A preferred compound for use in this method is Compound 1.

Some compounds exhibit plant growth regulating activity and may be deployed for this purpose, again at appropriate rates of application.

Therefore, in yet another aspect the invention provides a method of regulating plant growth which comprises applying to a plant, to a seed of a plant or to the locus of the plant or seed an effective amount of a compound as hereindefined or a composition containing the same. A preferred group of compounds for use in this aspect of the invention are compounds of formula (I) where X is hydrogen or $C_{1-4}$ alkoxy; V is oxygen; and $R^1$, $R^2$, W, Y and Z are hydrogen.

The compounds may be used directly for agricultural purposes but are more conveniently formulated into compositions using a carrier or diluent. The invention thus provides fungicidal, plant growth regulator, insecticidal and miticidal compositions comprising a compound as hereinbefore defined, and an acceptable carrier or diluent therefor.

The compounds can be applied in a number of ways. For example they can be applied, formulated or unformulated, directly to the foliage of a plant, to seeds or to other medium in which plants are growing or are to be planted, or they can be sprayed on, dusted on or applied as a cream or paste formulation, or they can be applied as a vapour or as slow release granules. Application can be to any part of the plant including the foliage, stems, branches or roots, or to soil surrounding the roots, or to the seed before it is planted; or to the soil generally, to paddy water or to hydroponic culture systems. The invention compounds may also be injected into plants or sprayed onto vegetation using electrodynamic spraying techniques or other low volume methods.

The term "plant" as used herein includes seedlings, bushes and trees. Furthermore, the fungicidal method of the invention includes preventative protectant, prophylactic and eradicant treatment.

The compounds are preferably used for agricultural and horticultural purposes in the form of a composition. The type of composition used in any instance will depend upon the particular purpose envisaged.

The compositions may be in the form of dustable powders or granules comprising the active ingredient (invention compound) and a solid diluent or carrier, for example fillers such as kaolin, bentonite, kieselguhr, dolomite, calcium carbonate, talc, powdered magnesia, Fuller's earth, gypsum, diatomaceous earth and China clay. Such granules can be preformed granules suitable for application to the soil without further treatment. These granules can be made either by impregnating pellets of filler with the active ingredient or by pelleting a mixture of the active ingredient and powdered filler. Compositions for dressing seed may include an agent (for example a mineral oil) for assisting the adhesion of the composition to the seed; alternatively the active ingredient can be formulated for seed dressing purposes using an organic solvent (for example N-methylpyrrolidone, propylene glycol or N,N-dimethylformamide). The compositions may also be in the form of wettable powders or water dispersible granules comprising wetting or dispersing agents to facilitate the dispersion in liquids. The powders and granules may also contain fillers and suspending agents.

Emulsifiable concentrates or emulsions may be prepared by dissolving the active ingredient in an organic solvent optionally containing a wetting or emulsifying agent and then adding the mixture to water which may also contain a wetting or emulsifying agent. Suitable organic solvents are aromatic solvents such as alkylbenzenes and alkylnaphthalenes, ketones such as isophorone, cyclohexanone, and methylcyclohexanone, chlorinated hydrocarbons such as chlorobenzene and trichlorethane, and alcohols such as benzyl alcohol, furfuryl alcohol, butanol and glycol ethers.

Suspension concentrates of largely insoluble solids may be prepared by ball or bead milling with a dispersing agent and including a suspending agent to stop the solid settling.

Compositions to be used as sprays may be in the form of aerosols wherein the formulation is held in a container under pressure in the presence of a propellant, eg. fluorotrichloromethane or dichlorodifluoromethane.

The invention compounds can be mixed in the dry state with a pyrotechnic mixture to form a composition suitable for generating in enclosed spaces a smoke containing the compounds.

Alternatively, the compounds may be used in microencapsulated form. They may also be formulated in biodegradable polymeric formulations to obtain a slow, controlled release of the active substance.

By including suitable additives, for example additives for improving the distribution, adhesive power and resistance to rain on treated surfaces, the different compositions can be better adapted for various utilities.

The invention compounds can be used as mixtures with fertilisers (eg. nitrogen-, potassium- or phosphorus-containing fertilisers). Compositions comprising only granules of fertiliser incorporating, for example coated with, the compound are preferred. Such granules suitably contain up to 25% by weight of the compound. The invention therefore also provides a fertiliser composition comprising a fertiliser and the compound of general formula (I) or a salt or metal complex thereof.

Wettable powders, emulsifiable concentrates and suspension concentrates will normally contain surfactants eg. a wetting agent, dispersing agent, emulsifying agent or suspending agent. These agents can be cationic, anionic or non-ionic agents.

Suitable cationic agents are quaternary ammonium compounds, for example cetyltrimethylammonium bromide. Suitable anionic agents are soaps, salts of aliphatic monoesters of sulphuric acid (for example sodium lauryl sulphate), and salts of sulphonated aromatic compounds (for example sodium dodecylbenzenesulphonate, sodium, calcium or ammonium lignosulphonate, butylnaphthalene sulphonate, and a mixture of sodium diisopropyl- and triisopropyl-naphthalene sulphonates).

Suitable non-ionic agents are the condensation products of ethylene oxide with fatty alcohols such as oleyl or cetyl alcohol, or with alkyl phenols such as octyl- or nonyl-phenol and octylcresol. Other non-ionic agents are the partial esters derived from long chain fatty acids and hexitol anhydrides, the condensation products of the said partial esters with ethylene oxide, and the lecithins. Suitable suspending agents are hydrophilic colloids (for example polyvinylpyrrolidone and sodium carboxymethylcellulose), and swelling clays such as bentonite or attapulgite.

Compositions for use as aqueous dispersions or emulsions are generally supplied in the form of a concentrate containing a high proportion of the active ingredient, the concentrate being diluted with water before use. These concentrates should preferably be able to withstand storage for prolonged periods and after such storage be capable of dilution with water in order to form aqueous preparations which remain homogeneous for a sufficient time to enable them to be applied by conventional spray equipment. The concentrates may conveniently contain up to 95%, suitably 10-85%, for example 25-60%, by weight of the active ingredient. After dilution to form aqueous preparations, such preparations may contain varying amounts of the active ingredient depending upon the intended purpose, but an aqueous preparation containing 0.0005% or 0.01% to 10% by weight of active ingredient may be used.

The compositions of this invention may contain other compounds having biological activity, eg. compounds having similar or complementary fungicidal activity or which plant possess plant growth regulating, herbicidal or insecticidal activity.

A fungicidal compound which may be present in the composition of the invention may be one which is capable of combating ear diseases of cereals (eg. wheat) such as Septoria, Gibberella and Helminthosporium spp., seed and soil-borne diseases and downy and powdery mildews on grapes and powdery mildew and scab on apple etc. By including another fungicide, the composition can have a broader spectrum of activity than the compound of general formula (I) alone. Further the other fungicide can have a synergistic effect on the fungicidal activity of the compound of general formula (I). Examples of fungicidal compounds which may be included in the composition of the invention are cabendazim, benomyl, thiophanate-methyl, thiabendazole, fuberidazole, etridazole, dichlofluanid, cymoxanil, oxadixyl, ofurace, metalaxyl, furalaxyl, benalaxyl, fosetyl-aluminium, fenarimol, iprodione, prothiocarb, procymidone, vinclozolin, penconazole, myclobutanil, propamocarb, R0151297, diniconazole, pyrazophos, ethirimol, ditalimfos, tridemorph, triforine, nuarimol, triazbutyl, guazatine, triacetate salt of 1,1'-iminodi(octamethylene)diguanidine, buthiobate, propiconazole, prochloraz, flutriafol, hexaconazole, (2 RS, 3 RS)-2-(4-chlorophenyl)-3-cyclopropyl-1-(1H-1,2,4-triazol-1-yl)butan-2-ol, (RS)-1-(4-chlorophenyl)-4,4-dimethyl-3-(1H-1,2,4-triazol-1-ylmethyl)pentan-3-ol, fluzilazole, triadimefon, triadimenol, diclobutrazol, fenpropimorph, pyrifenox, fenpropidin, chlorozolinate, imazalil, fenfuram, carboxin, oxycarboxin, methfuroxam, dodemorph, BAS 454, blasticidin S, kasugamycin, edifenphos, Kitazin P, cycloheximide, phthalide, probenazole, isoprothiolane, tricyclazole, 4-chloro-N-(cyano(ethoxy)methyl)benzamide, pyroquilon, chlobenzthizone, neoasozin, polyoxin D, validamycin A, mepronil, flutolanil, pencycuron, dichlomezine, phenazin oxide, nickel dimethyldithiocarbamate, techlofthalam, bitertanol, bupirimate, etaconazole, hydroxyisoxazole, streptomycin, cyprofuram, biloxazol, quinomethionate, dimethirimol, 1-(2-cyano-2-methoxyiminoacetyl)-3-ethyl urea, fenapanil, tolclofos-methyl, pyroxyfur, polyram, maneb, mancozeb, captafol, chlorothalonil, anilazine, thiram, captan, folpet zineb, propineb, sulphur, dinocap, dichlone, chloroneb, binapacryl, nitrothal-isopropyl, dodine, dithianon, fentin hydroxide, fentin acetate, tecnazene, quintozene, dicloran, copper containing compounds such as copper oxychloride, copper sulphate and Bordeaux mixture, and organomercury compounds. The compounds of general formula (I) can be mixed with soil, peat or other rooting media for the protection of plants against seed-borne, soil-borne or foliar fungal diseases.

Suitable insecticides which may be incorporated in the composition of the invention include pirimicarb, dimethoate, demeton-s-methyl, formothion, carbaryl, isoprocarb, XMC, BPMC, carbofuran, carbosulfan, diazinon, fenthion, fenitrothion, phenthoate, chlorpyrifos, isoxathion, propaphos, monocrotophas, buprofezin, ethroproxyfen and cycloprothrin.

Plant growth regulating compounds are compounds which control weeds or seedhead formation, or selectively control the growth of less desirable plants (eg. grasses).

Examples of suitable plant growth regulating compounds for use with the invention compounds are the gibberellins (eg. $GA_3$, $GA_4$ or $GA_7$), the auxins (eg. indoleacetic acid, indolebutyric acid, naphthoxyacetic acid or naphthylacetic acid), the cytokinins (eg. kinetin, diphenylurea, benzimidazole, benzyladenine or benzylaminopurine), phenoxyacetic acids (eg. 2,4-D or MCPA), substituted benzoic acid (eg. triiodobenzoic acid), morphactins (eg. chlorfluoroecol), maleic hydrazide, glyphosate, glyphosine, long chain fatty alcohols and acids, dikegulac, paclobutrazol, fluoridamid, mefluidide, substituted quaternary ammonium and phosphonium compounds (eg. chloromequat chlorphonium or mepiquatchloride), ethephon, carbetamide, methyl-3,6-dichloroanisate, daminozide, asulam, abscisic acid, isopyrimol, 1-(4-chlorophenyl)-4,6-dimethyl-2-oxo-1,2-dihydropyridine-3-carboxylic acid, hydroxybenzonitriles (eg. bromoxynil), difenzoquat, benzoylprop-ethyl 3,6-dichloropicolinic acid, fenpentezol, inabenfide, triapenthenol and tecnazene.

The following Examples illustrate the invention. Throughout these examples magnesium sulphate was used to dry solutions, and reactions involving water sensitive intermediates were performed under an atmosphere of nitrogen and in dried solvents. The following abbreviations are used:
g=gramme(s)
ml=milliliter(s)
THF=tetrahydrofuran
DMF=N,N'-dimethylformamide
ether=diethyl ether
m.p.=melting point

EXAMPLE 1

This Example illustrates the preparation of (Z)-methyl 3-methoxy-2-[6-ethoxyindol-1-yl]acrylate. (Compound No 2 of Table I).

Potassium tert-butoxide (0.77 g, 6.9 mmol) was stirred with dry ether (50 ml) containing 18-crown-6 (0.164 g, 0.62 mmol). 6-Ethoxyindole (1.0 g, 6.2 mmol) was added portionwise over 15 minutes at room temperature. This was stirred for ½ hour then cooled to 0° C. when methyl bromoacetate (0.65 ml, 6.9 mmol) in ether (5 ml) was added dropwise. The reaction mixture was stirred for 16 hours at room temperature then poured into water (150 ml) and extracted with ether (2×100 ml). The extracts were washed with brine (2×75 ml), dried and concentrated to give crude methyl(6-ethoxyindol-1-yl)acetate (1.4 g, 96% yield) as a brown oil.

Sodium hydride (0.58 g, 50% in oil, 12 mmol) was washed with petrol (60°-80° C.) and suspended in DMF (20 ml). To this, with vigorous stirring, was added dropwise, a solution of the crude methyl(6-ethoxyindol-1-yl)acetate (1.4 g, 6 mmol) and methyl formate (1.8 ml, 30 mmol) in DMF (10 ml) at room temperature. After 3 hours the reaction mixture was poured into 10% aqueous potassium carbonate (100 ml), washed with ether (2×100 ml), neutralised with concentrated hydrochloric acid and extracted with ether (2×100 ml). These extracts were washed with brine, dried and concentrated to give methyl 3-hydroxy-2-(6-ethoxyindol-1-yl)acrylate (1.0 g, 63% yield) as an orange oil.

To a stirred suspension of potassium carbonate (1.1 g, 8 mmol) in DMF (30 ml), the methyl 3-hydroxy-2-(6-ethoxyindol-1-yl)acrylate (1.0 g, 3.8 mmol) in DMF (10 ml) was added dropwise. After stirring for 15 minutes at room temperature, dimethyl sulphate (0.36 ml, 3.8 mmol) was added dropwise. The resulting mixture was stirred for 2½ hours then poured into brine (100 ml) and extracted with ether (3×100 ml). The extracts were washed with brine, dried and concentrated under reduced pressure to give an orange oil. Purification by column chromatography using silica gel with ether as the eluant gave the title compound (0.4 g, 38% yield) as a white crystalline solid melting at 91°-2° C.

EXAMPLE 2

This Example illustrates the preparation of (Z)-methyl 3-methoxy-2-[6-phenylindol-1-yl]acrylate (Compound No. 3 of Table I).

Phenyllithium (10 ml of a 2.0M solution in a 7:3 mixture of cyclohexane and ether, 20 mmol) was added dropwise to zinc chloride (20 ml of a 1.0M solution in ether, 20 mmol) at room temperature. The resulting mixture was stirred for 2 hours, then a solution of 4-iodo-2-nitrotoluene (2.63 g, 10 mmol) in THF (20 ml) and tetrakis(triphenylphosphine)palladium (0.3 g, 0.26 mmol) were added successively. The reaction mixture was stirred for 3 hours then diluted with 0.5M hydrochloric acid (40 ml) and extracted with ether (3×70 ml). The ether extracts were washed with brine, dried, concentrated then purified by column chromatography using petrol (60°-80° C.)-ethyl acetate (9:1) on silica gel to give 4-phenyl-2-nitrotoluene (1.8 g, 85% yield) as a yellow oil.

A mixture of 4-phenyl-2-nitrotoluene (1.8 g, 8.5 mmol), N,N-dimethylformamide dimethyl acetal (4.4 ml, 33 mmol) and pyrrolidine (0.78 ml, 9.3 mmol) was heated in DMF (20 ml) at 110° C. for 16 hours. The resulting deep red solution was poured into water (100 ml) and extracted with ether (2×100 ml). These extracts were concentrated to give a deep red oil which was dissolved in acetone (5 ml) and then added to a mixture of titanium(III) chloride (40.4 g of a 20% solution in aqueous hydrochloric acid, 52 mmol) and ammonium acetate (80 ml of a 3.9M aqueous solution). The resulting mixture was shaken for 10 minutes and then extracted with ether (3×100 ml). The extracts were washed with brine, dried and concentrated to give a dark solid, which was crystallised from a mixture of petrol (60°-80° C.) and dichloromethane to give 6-phenylindole (1.16 g, 71% yield) as a dark crystalline solid melting at 154° C. (Literature m.p. 160°-1° C., O.Sus et al, *Justus Liebigs Ann. Chem.*, 1955, 593, 91).

6-Phenylindole (0.57 g, 3.0 mmol), was converted into the title compound (0.24 g, 26% yield) in the 3 steps described in Example 1, that is by treatment with potassium tert-butoxide and methyl bromoacetate followed by formylation with sodium hydride and methyl formate and subsequent methylation with potassium carbonate and dimethyl sulphate. The title compound is an almost white solid melting at 158-160° C.

The following are examples of compositions suitable for agricultural and horticultural purposes which can be formulated from the compounds of the invention. Such compositions form another aspect of the invention. Percentages are by weight.

EXAMPLE 3

An emulsifiable concentrate is made up by mixing the ingredients, and stirring the mixture until all the constituents are dissolved.

| | |
|---|---|
| Compound of Example 1 | 10% |
| Benzyl alcohol | 30% |
| Calcium dodecylbenzenesulphonate | 5% |
| Nonylphenolethoxylate (13 moles ethylene oxide) | 10% |
| Alkyl benzenes | 45% |

EXAMPLE 4

The active ingredient is dissolved in methylene dichloride and the resultant liquid sprayed onto the granules of attapulgite clay. The solvent is then allowed to evaporate to produce a granular composition.

| | |
|---|---|
| Compound of Example 1 | 5% |
| Attapulgite granuales | 95% |

EXAMPLE 5

A composition suitable for use as a seed dressing is prepared by grinding and mixing the three ingredients.

| | |
|---|---|
| Compound of Example 1 | 50% |
| Mineral oil | 2% |
| China clay | 48% |

EXAMPLE 6

A dustable powder is prepared by grinding and mixing the active ingredient with talc.

| | |
|---|---|
| Compound of Example 1 | 5% |
| Talc | 95% |

EXAMPLE 7

A suspension concentrate is prepared by ball milling the constituents set out below, to form an aqueous suspension of the ground mixture with water.

| | |
|---|---|
| Compound of Example 1 | 40% |
| Sodium lignosulphonate | 10% |
| Bentonite clay | 1% |
| Water | 49% |

This formulation can be used as a spray by diluting into water or applied directly to seed.

EXAMPLE 8

A wettable powder formulation is made by mixing and grinding together the ingredients below:

| | |
|---|---|
| Compound of Example 1 | 25% |
| Sodium lauryl sulphate | 2% |
| Sodium lignosulphonate | 5% |
| Silica | 25% |
| China clay | 43% |

EXAMPLE 9

This Example illustrates the fungicidal properties of compounds 1 to 4, 7 and 8 when tested against a variety of foliar fungal diseases of plants. The technique employed was as follows.

The plants were grown in John Innes Potting Compost (No 1 or 2) in 4 cm diameter minipots. The test compounds were formulated either by bead milling with aqueous Dispersol T or as a solution in acetone or acetone/ethanol which was diluted to the required concentration immediately before use. For the foliage diseases, the formulations (100 ppm active ingredient) were sprayed on to the foliage and applied to the roots of the plants in the soil. The sprays were applied to maximum retention and the root drenches to a final concentration equivalent to approximately 40 ppm a.i./dry soil. Tween 20, to give a final concentration of 0.05%, was added when the sprays were applied to cereals.

For most of the tests the compounds were applied to the soil (roots) and to the foliage (by spraying) one or two days before the plant was inoculated with the disease. An exception was the test on Erysiphe graminis in which the plants were inoculated 24 hours before treatment. Foliar pathogens were applied by spray as spore suspensions onto the leaves of test plants. After inoculation, the plants were put into an appropriate environment to allow infection to proceed and then incubated until the disease was ready for assessment. The period between inoculation and assessment varied from four to fourteen days according to the disease and environment.

The disease control was recorded by the following grading:
4 = no disease
3 = trace—5% of disease on untreated plants
2 = 6–25% of disease on untreated plants
1 = 26–59% of disease on untreated plants
0 = 60–100% of disease on untreated plants The results are shown in Table III.

TABLE III

| COMPOUND NO. | ERYSIPHE GRAMINIS (BARLEY) | VENTURIA INAEQUALIS (APPLE) | PYRICULARIA ORYZAE (RICE) | CERCOSPORA ARACHIDICOLA (PEANUT) | PLASMORPARA VITICOLA (VINE) | PUCCINIA RECONDITA (WHEAT) | PHYTOPHTHORA INFESTANS (TOMATO) |
|---|---|---|---|---|---|---|---|
| 1 | 1 | 3 | 3 | 3 | 4 | 0 | — |
| 2 | 4 | 4 | 4 | 4 | 4 | 4 | 4 |
| 3 | 2 | 4 | 4 | — | 4 | 4 | 4 |
| 4 | 2 | 4 | 4 | 3 | 4 | 1 | 0 |
| 7 | 4 | 4 | — | 4 | 4 | 4 | 4 |
| 8 | 4 | 4 | — | 4 | 4 | 4 | 4 |

EXAMPLE 10

This Example illustrates the plant growth regulating properties of compounds 1 and 2 when tested on a whole plant screen against various species of plant. The plant species are identified in Table IV with the leaf stage at which they were sprayed.

A formulation of each chemical was applied at 4000 ppm (4 kg/ha in a 1000 l/ha field volume) using a track-sprayer and a SS8004E (Teejet) nozzle.

After spraying, the plants were grown in a glasshouse with 25° C. day/22° C. night temperatures. Supplementary lighting was supplied when necessary to provide an average photoperiod of 16 hours (14 hours minimum).

After 2-6 weeks in the glasshouse, depending on species and time of year, the plants were visually assessed for morphological characteristics against a control plant sprayed with a blank formulation. The results are presented in Table V.

TABLE IV

| | PLANT MATERIAL USED FOR WHOLE PLANT SCREEN | | | |
|---|---|---|---|---|
| SPECIES | CODE | VARIETY | GROWTH STAGE AT TREATMENT | NO. PLANTS PER 3" POT | COMPOST TYPE |
| Maize | MZ | Earliking | 2¼-2½ leaves | 1 | PEAT |
| Apple | AP | Red Delicious | 4-5 leaves | 1 | JIP* |
| Rice | RC | Ishikari | 2-2½ leaves | 4 | JIP |
| Tomato | TO | Ailsa Craig | 2-2½ leaves | 1 | PEAT |

*John Innes Potting Compost.

TABLE V

| PLANT MATERIAL | COMPOUND NO. | R | G | A | T | I | P |
|---|---|---|---|---|---|---|---|
| RC | 1 | 1 | | | | 1 | |
| RC | 2 | | | | | | |
| AP | 1 | 1 | | | | 1 | |
| TO | 2 | 3 | | 3 | 1 | 3 | 2 |
| MZ | 1 | | | | | | |
| MZ | 2 | | 1 | 2 | | | |

Key:
R = Retardation
G = Greening effect
A = Apical damage
T = Tillering or side shooting
I = Interligular or internodal length reduction
P = Phytotoxicity
All effects, except phytotoxicity, are scored visually on a 1-3 basis where
1 = 10-30%
2 = 31-60%
3 = 61-100%
Blank means less than 10% effect.
Phytotoxicity is scored on a 1-5 basis where
1 = less than 10%
2 = 11-30%
3 = 31-50%
4 = 51-70%
5 = greater than 70%
Blank mean no effect at all observed.

This Example illustrates the insecticidal properties of compound 1.

The activity of the compound was determined using insect, mite and nematode pests. The compound was used in the form of a liquid preparation containing 500 parts per million (ppm) by weight of the compound except for the test on *Meloidogyne incognita* when a liquid preparation of 250 ppm by weight was used. The preparation was made by dissolving the compound in acetone and diluting the solution with water containing 0.1% by weight of a wetting agent sold under the trade name "SYNPERONIC" NX until the liquid preparation contained the required concentration of the product. "SYNPERONIC" is a Registered Trade Mark.

The test procedure adopted with regard to each pest was basically the same and comprised supporting a number of the pests on a medium which was usually a host plant or a foodstuff on which the pests feed, and treating either or both the pests and the medium with the preparation. The mortality of the pests was then assessed at periods usually varying from one to seven days after the treatment.

The results of the tests are given in Table VII as a grading of mortality designated as 9, 5 or 0 wherein 9 indicates 80-100% mortality, 5 indicates 50-79% mortality and 0 indicates less than 50% mortality.

In Table V the pest organism used is designated by a letter code and the pests species, the support medium or food, and the type and duration of test is given in Table VI.

The knockdown properties of compound 1 against *Musca domestica* was demonstrated as follows.

A sample of compound 1 was diluted with 2 mls acetone and made up of a 2000 ppm solution with 0.1% aqueous synperonic solution. The solution (1 ml) was then sprayed directly onto twenty mixed sex houseflies held in a drinking cup. Immediately after spraying the cups were inverted and left to dry. An assessment of knockdown was made when the cups were righted 15 minutes later. The flies were then provided with a 10% sucrose solution on a cotton wool pad, and held for 48 hours in a holding room conditioned at 25° C. and 65% relative humidity before a mortality assessment was made.

TABLE VI

| CODE LETTERS (TABLE IV) | TEST SPECIES | SUPPORT MEDIUM/FOOD | TYPE OF TEST | DURATION (DAYS) |
|---|---|---|---|---|
| TUa | *Tetranychus urticae* (spider mites - adults) | French bean leaf | Contact | 3 |
| TUe | *Tetranychus urticae* (spider mites - ova) | French bean leaf | Contact | 6 |
| MP | *Myzus persicae* (aphids) | Chinese Cabbage leaf | Contact | 3 |
| NL | *Nilaparvata lugens* (brown plant hopper - nymphs) | Rice plant | Contact | 3 |
| HV | *Heliothis virescens* (tobacco budworm - larvae) | Cotton leaf | Residual | 3 |
| DB | *Diabrotica balteata* (rootworm larvae) | Filter paper/maize seed | Residual | 3 |
| BG | *Blattella germanica* (cockroach nymphs) | Plastic pot | Residual | 3 |
| MDa | *Musca domestica* (houseflies - adults) | Cotton wool/sugar | Contact | 1 |

TABLE VI-continued

| CODE LETTERS (TABLE IV) | TEST SPECIES | SUPPORT MEDIUM/FOOD | TYPE OF TEST | DURATION (DAYS) |
|---|---|---|---|---|
| MDk | *Musca domestica* (houseflies - adults) | Inverted cup | knockdown | 2 |
| MI | *Meloidogyne incognita* (tomato root knot eelworm - larvae) | Semi in-vitro | Residual | 7 |
| CPA | *Chilo partellus* (maize and sorghum stem borers - larvae) | Oilseed rape | Residual | 3 |

"Contact" test indicates that both pests and medium were treated and "residual" indicates that the medium was treated before infestation with the pests.

TABLE VII

| COMPOUND NO. | TUa | TUe | MP | NL | MDa | MDk | HV | DB | MI | CPA | BG |
|---|---|---|---|---|---|---|---|---|---|---|---|
| 1 | 9 | 0 | 0 | 0 | 0 | 0 | 0 | 0 | 0 | 9 | 0 |

We claim:

1. A compound of the formula (I):

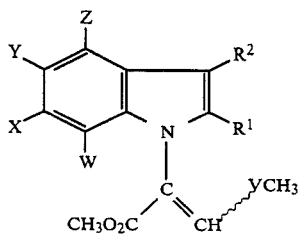

or a stereoisomer thereof, wherein $R^1$ and $R^2$, which are the same or different are hydrogen, cyano, halogen or $C_{1-6}$ alkyl; V is oxygen or sulphur; W, X, Y and Z, which may be the same or different, are hydrogen, halogen, nitro, cyano, $C_{1-6}$ alkyl, $C_{3-6}$ cycloalkyl, $C_{3-6}$ cycloalkyl($C_{1-6}$)alkyl, phenyl($C_{1-4}$)alkyl, phenyl, phenoxy, $C_{1-6}$ alkoxy, phenyl($C_{1-4}$)alkoxy, $C_{2-6}$ alkenyl, $C_{2-6}$ alkenyl substituted with phenyl or an aromatic 5- or 6-membered heterocyclic ring containing at least one nitrogen, sulphur or oxygen heteroatom, $S(O)_nR^3$ (wherein n is 0, 1 or 2), or an aromatic 5- or 6-membered heterocyclic ring containing at least one nitrogen, sulphur or oxygen heteroatom, or W, X, or X, Y or Y, Z together form methylenedioxy; and $R^3$ is $C_{1-6}$ alkyl, phenyl, phenyl($C_{1-4}$)alkyl or an aromatic 5- or 6-membered heterocyclic ring containing at least one nitrogen, sulphur or oxygen atom; wherein any of the foregoing alkyl, cycloalkyl, cycloalkylalkyl and alkoxy groups and the alkyl moieties of phenylalkyl and phenylalkoxy groups may be substituted with hydroxy, halogen, $C_{1-4}$ alkoxy or $C_{1-4}$ alkoxycarbonyl, and wherein any of the foregoing phenyl groups, the phenyl moieties of phenylalkyl, phenylalkoxy and phenoxy groups or heterocyclic rings may be substituted with halogen, hydroxy, $C_{1-4}$ alkyl, trifluoromethyl, $C_{1-4}$ alkoxy or trifluoromethoxy.

2. A compound of formula (Ia):

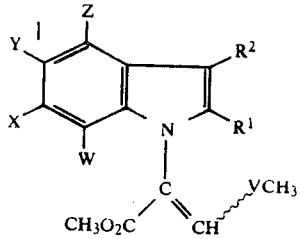

or a stereoisomer thereof, wherein $R^1$ and $R^2$, which are the same or different, are hydrogen, cyano, halogen or $C_{1-6}$ alkyl; W, Y and Z, which may be the same or different, are hydrogen, halogen, nitro, cyano, $C_{1-6}$ alkyl, $C_{1-6}$ alkoxy, $C_{2-6}$ alkenyl, $C_{2-6}$ alkenyl substituted with phenyl or an aromatic 5- or 6-membered heterocyclic ring containing at least one nitrogen, sulphur or oxygen heteroatom; and X is phenyl, an aromatic 5- or 6-membered heterocyclic ring containing at least one nitrogen, sulphur or oxygen heteroatom, or phenoxy; or W, X or X, Y or Y and Z together form methylendioxy; wherein any of the foregoing alkyl and alkoxy groups may be substituted with hydroxy, halogen, $C_{1-4}$ alkoxy or $C_{1-4}$ alkoxycarbonyl and wherein any of the foregoing phenyl groups, the phenyl moiety of the phenoxy group or heterocyclic rings may be substituted with halogen, hydroxy, $C_{1-4}$ alkyl, trifluoromethyl, $C_{1-4}$ alkoxy or trifluoromethoxy.

3. The (Z)-isomer of a compound according to claim 1 or 2.

4. A fungicidal composition comprising as an active ingredient an effective amount of a compound according to claim 1 and a fungicidally acceptable diluent or carrier therefor.

5. A method of combatting fungi which comprises applying to a plant, to a seed of a plant or to the locus of the plant or seed, a fungicidally effective amount of a compound according to claim 1.

6. A plant growth regulator composition comprising an effective amount of a compound according to claim 1 and a diluent or carrier therefor.

7. A method of regulating plant growth which comprises applying to a plant, to a seed of a plant or to the locus of the plant or seed, an effective amount of a compound according to claim 1.

8. An insecticidal or miticidal composition comprising an effective amount of a compound according to claim 1 and a carrier or diluent therefor.

9. A method of killing or controlling insect or mite pests which comprises administering to the pest or locus thereof an effective amount of a compound according to claim 1.

* * * * *